United States Patent [19]

Parker

[11] Patent Number: 5,745,365
[45] Date of Patent: Apr. 28, 1998

[54] WEB MONITORING FOR PAPER MACHINES

[75] Inventor: John Russell Parker, Gravesend, Great Britain

[73] Assignee: John Heyer Paper Ltd., Aylesford, Great Britain

[21] Appl. No.: 750,500

[22] PCT Filed: May 26, 1995

[86] PCT No.: PCT/GB95/01222

§ 371 Date: May 7, 1997

§ 102(e) Date: May 7, 1997

[87] PCT Pub. No.: WO95/34810

PCT Pub. Date: Dec. 21, 1995

[30] Foreign Application Priority Data

Jun. 14, 1994 [GB] United Kingdom ............... 9411908

[51] Int. Cl.⁶ ................................................ G06F 19/00
[52] U.S. Cl. .............. 364/469.01; 162/263; 364/471.03
[58] Field of Search ............................ 364/469.01, 471.01,
364/471.02, 471.03, 572, 576, 560, 551.01;
250/559.05, 559.06, 559.39, 559.4, 559.45,
559.46, 559.48; 356/429–431; 162/252,
253, 262, 263, DIG. 10, 198

[56] References Cited

U.S. PATENT DOCUMENTS

| | | |
|---|---|---|
| 4,910,688 | 3/1990 | Amini . |
| 4,947,684 | 8/1990 | Balakrishnan . |
| 5,118,195 | 6/1992 | Dobbie . |
| 5,381,341 | 1/1995 | Herrala et al. ............... 364/471.03 |
| 5,400,258 | 3/1995 | He ............................... 364/471.03 |
| 5,539,634 | 7/1996 | He ............................ 364/471.03 X |
| 5,563,809 | 10/1996 | Williams et al. ......... 364/471.03 X |

FOREIGN PATENT DOCUMENTS

| | | |
|---|---|---|
| 0 052 813 A2 | 6/1982 | European Pat. Off. . |
| 0 316 961 A2 | 5/1989 | European Pat. Off. . |
| WO 91/05105 | 4/1991 | WIPO . |

OTHER PUBLICATIONS

PCT International Search Report PCT/GB 95/01222 Sep. 28, 1995.

*Primary Examiner*—Joseph Ruggiero
*Attorney, Agent, or Firm*—Wallenstein & Wagner, Ltd.

[57] ABSTRACT

An apparatus for web monitoring in paper making machines comprises a row of two or more lookers (6, 8) which are spaced across the width of the moving paper web. Each looker is stationery, and continuously inspects one or more small areas of the web as the web passes beneath. Optical signals from each individual inspection area are digitized, and spatial filtering is used to remove from the signals the effects of variations in the web which are much larger or much smaller than the variations being studied. A number of power spectra are calculated from the spatially filtered signals, and analysis of these functions is then used to identify significant features. Plots or tables of such features can be used to provide detailed information for the machine operator on the types of variations that are occurring in the paper web, and the possible causes of these variations.

23 Claims, 10 Drawing Sheets

(a) FLOCCULATION
(b) MACRO FORMING FAULTS
(c) UNSTABLE STREAKS
(d) 'BARS' CAUSED BY HIGH FREQUENCY PERIODIC DISTURBANCES
(e) SLOW VARIATION FROM THE WET END
(f) EVENTS (NOT SHOWN)

FIG. 4
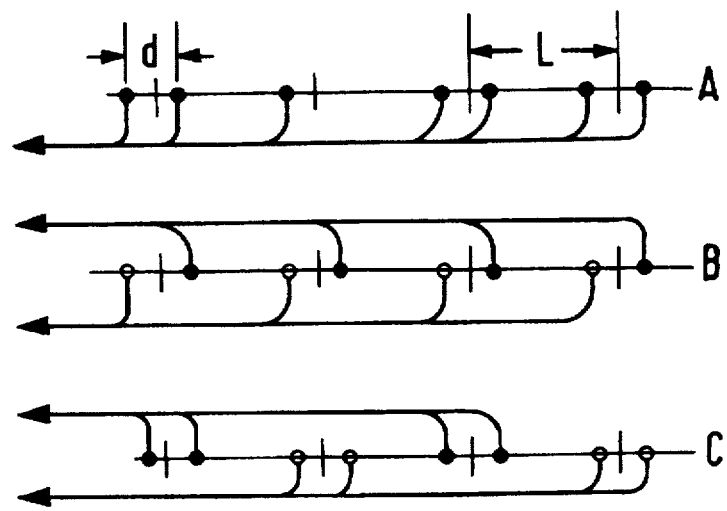
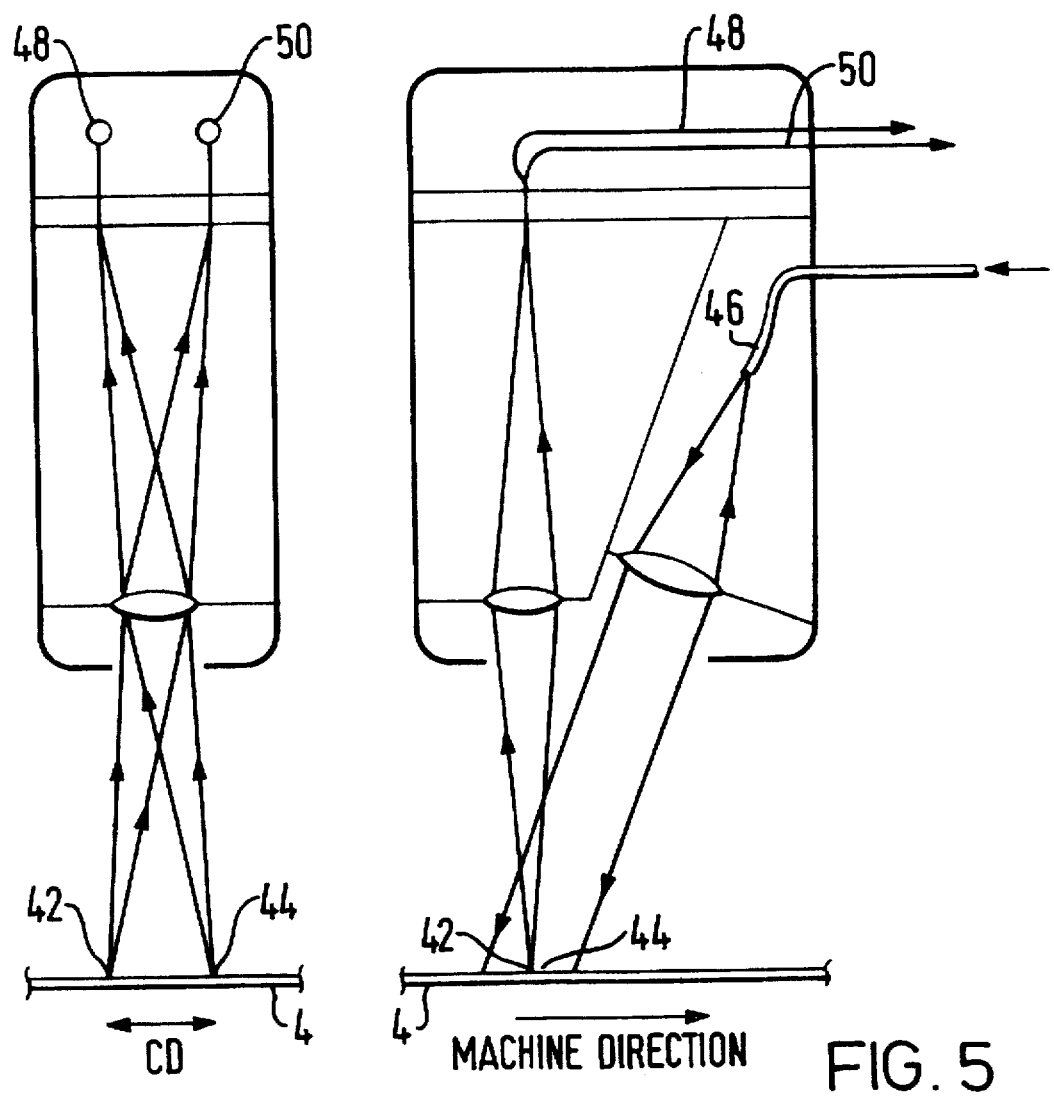
FIG. 5

FIG. 6
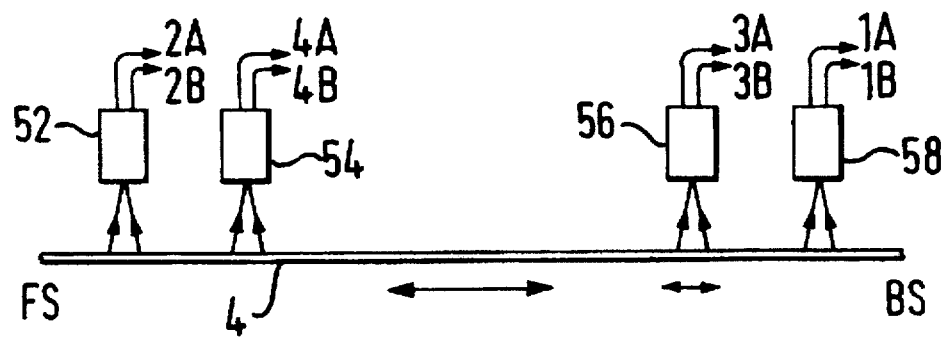
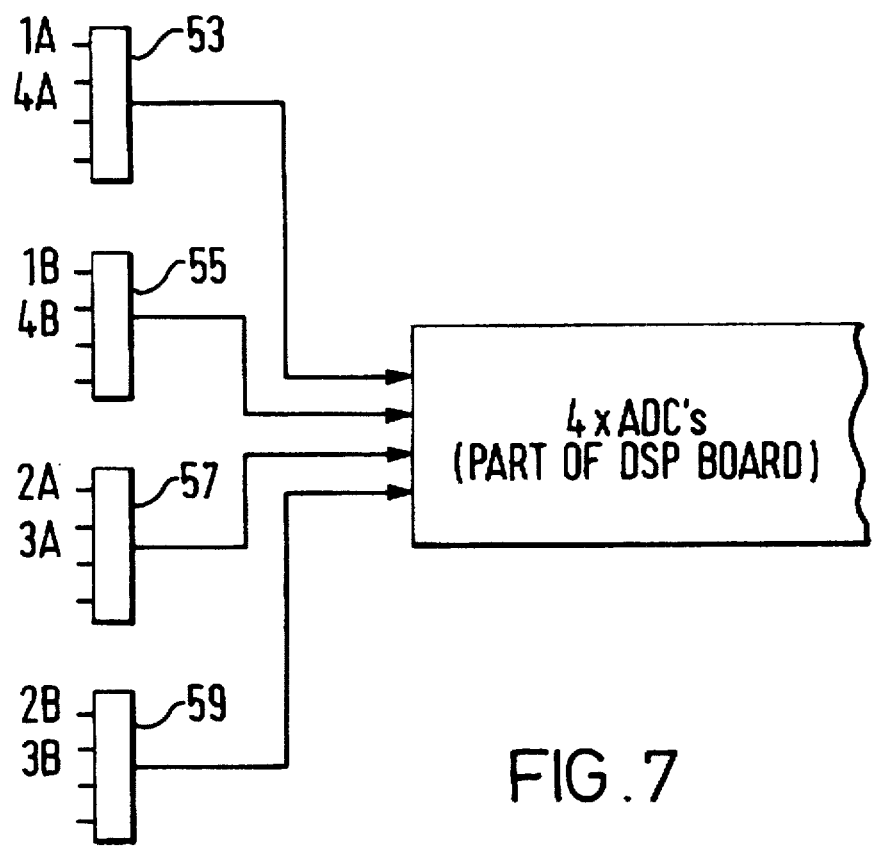
FIG. 7

WEB MONITORING FOR PAPER MACHINES

The present invention relates to a method of and apparatus for web monitoring in paper making machines.

Paper making machines are complicated mechanical systems which are susceptible to a large number of problems, some of which can affect the quality or the consistency of the paper which is being produced. Looked at from one perspective, a paper machine can be thought of as a gigantic multi-channel tape recorder. The effects of mechanical vibrations, pulsations, control loop faults, non-uniform consistency of the pulp, together with a number of types of smaller scale random variation, all get written into the paper web. If not kept within bounds, they can affect the efficiency of the manufacturing process as well as the quality of the product. Their frequencies range from one cycle in about 6 minutes, or 0.003 Hz, up to almost 10,000 Hz.

In recent years, systems have become commercially available for permanent installation on paper machines to monitor the more common sources of disturbance.

Signal averaging is normally used to determine the contribution of the rotation of some roll, wet press felt or impeller either to the variations in the paper web or to the vibration of the end of a press roll.

Signal averaging, also known as signal extraction, is a method for discovering the contribution to some output signal of the cyclic variation associated with a steadily rotating or repeating source. To carry out signal averaging it is necessary to have a trigger signal in the form of a sharp pulse that indicates the commencement of each new rotation or repetition of the source of possible disturbance. When this trigger signal is received, sampling of the output signal is immediately commenced at a steady rate many times greater than repetition frequency of the source. Each sample is saved digitally in an array. The sampling continues until a further trigger pulse is received. It is then temporarily suspended. This process is repeated, with the difference that as each subsequent set of samples is obtained they are individually added to the values already saved in the array. After 100 or so sets of samples have been summed sampling ceases and each sum saved in the array is divided by the number of sets of samples taken, in order to obtain a time series representing the mean contribution of the input signal to the output.

Signal averaging works well within its limitations. It is only applicable to periodic inputs for which trigger signals can be obtained. It may be applied to rotating rolls and impellers, when it will give a result corresponding to the sum of the components of the output signal that have frequencies corresponding accurately to multiples of the trigger frequency. It will not detect the faults in the rollers of the bearings used to support the rotating element because these do not give rise to frequencies that are simple multiples of the trigger signal. It may be confused by periodic disturbances having harmonic frequencies that almost match the possible harmonic frequencies of the trigger signal. No statistical test has been devised to show whether or not the averaged signal has been contaminated by such unrelated periodics. It cannot, by its nature, be used to decide whether or not a randomly related signal is affecting another signal.

Before the introduction of the systems for permanent installation on paper machines, mentioned above, it was conventional to put sensors in place on an ad hoc basis and to take recordings, for example of the paper basis weight, for a total of several hours. Later these had to be analysed and studied off site in a laboratory for several days before the conclusions could be reported back to the mill. The long time required to report results was clearly a disadvantage, although it was accepted that considerable skill and experience was sometimes necessary to arrive at sound conclusions.

There are very many types of variation that can occur in paper webs, by no means all of which can currently be detected by conventional systems. FIG. 1 shows some examples of the patterns of variation which can occur, as follows:

(a) Flocculation (b) Macro forming faults (c) Unstable streaks (d) (i) Periodic variation caused by faults on the paper machine (d)(ii) Periodic variation caused by faults in auxiliary equipment.

(e) Random variations from the thin or thick stock systems (the "wet end")

(f) Events: bursts of variation caused by intermittent faults.

These examples will now be explained in rather more detail. For the sake of certainty, it should be understood that the "machine direction" (MD) is the direction parallel to movement of the paper web; the "cross direction" (CD) is the perpendicular direction across the paper web. One edge of the paper web is normally known as the "front side" (FS), and the other is known as the "back side" (ES); these relate to the front and back of the paper making machine, as it is seen by the operator.

(a) Flocculation is the clumping together of the fibres in the diluted pulp from which the paper web is formed; it causes small scale randomly distributed variations in the paper up to 15 mm across. (They can be seen in "look through" of any sheet of paper when it is held up against the light.) The importance of flocs will be better appreciated when it is realised that flocs, rather than paper fibres, can be regarded as the units from which any paper web is constructed. Flocculation is always present to some degree but can be controlled by various means.

(b) Macro forming faults are random defects, larger than flocs, caused by the mechanical disturbance of the pulp as it is being formed into paper. They have not previously been measured or systematically studied.

(c) Unstable machine direction steaks are thought to arise in the headbox from which the dilute pulp is discharged onto the wire of the paper machine. These take the form of sinuous machine direction lines of high or low basis weight which wander slowly to and fro across the machine. Their width is usually less than 20 mm.

(d) Periodic variations caused by mechanical faults are assigned to one of two classes, dependant on whether their causes are located on the machine or in auxiliary equipment. It is possible to distinguish between these categories because the speed of all paper machines is deliberately altered from time to time. Periodic frequencies that vary with speed are caused by some part of the machine itself. If they remain constant, or vary independently, they are from auxiliary equipment. In either case, a single source of variation might give rise to a several harmonics of its fundamental. The observed harmonically related components must therefore be examined to detect harmonically related components from a common source, then tabulated with frequency and amplitude. They tend to affect the full width of the web, and to have frequencies in the range 0.2–125 Hz.

(e) Slow, often random variations in the consistency (concentration) of the dilute pulp from which the paper web is formed may be caused by a variety of faults, either in the "approach flow" system design, or because of process control faults. They tend to affect the full width of the paper web, and to have frequencies between 0.003 and 1.0 Hz.

(f) Events (not shown in FIG. 1) are bursts of variation caused by intermittent faults. They may have durations from less than 0.01 second up to 30 seconds or more.

According to the present invention there is provided a method of analysing variations in a moving web characterised by:

(a) repeatedly or continuously sampling variations in a characteristic of the web (4) at each of a plurality of inspection locations (18,20,22,24) spaced apart across the web to produce a corresponding plurality of raw data signals;

(b) determining from the raw data signals a plurality of intermediate signals, at least one intermediate signal being representative of a weighted or unweighted additive or subtractive combination of two or more of the raw data signals;

(c) calculating a power spectrum for each of the intermediate signals;

(d) comparing a weighted or unweighted pair of said power spectra to produce a variation output; and (e) determining the variations in the sampled web characteristic according to the variation output.

According to a further aspect of the present invention there is provided apparatus for monitoring variations in a moving web characterised by:

(a) sampling means for repeatedly or continuously sampling variations in a characteristic of the web (4) at each of a plurality of inspection locations (18,20,22,24) spaced apart across the web to produce a corresponding plurality of raw data signals;

(b) determining means for determining from the raw data signals a plurality of intermediate signals, at least one intermediate signal being representative of a weighted or unweighted additive or subtractive combination of two or more of the raw data signals;

(c) operating means for calculating a power spectrum for each of the intermediate signals and for comparing a weighted or unweighted pair of said power spectra to produce a variation output; and (d) output calculation means for determining the variations in the sampled web characteristics according to the variation output.

The invention further extends to a paper making machine having apparatus for analysing variations in the moving paper web, as well as a method of analysing variations in the moving paper web of a paper making machine. The web to be sampled may be dry or wet paper, coated or uncoated, or may be some other material. The invention may also be generalised for use on other types of moving webs, such as textile webs or webs carrying printed material. It could also be used to monitor webs of other materials, such as plastics or sheet steel.

Dealing specifically with paper making machines, one of the main purposes of monitoring a paper machine is to detect and if possible to diagnose causes of variations affecting the paper web. Rather than attempt to monitor all the possible sources of disturbance, the present invention aims to monitor the paper web and to detect and automatically characterise the variations present in the paper so that their sources can readily be identified.

Preferably, the system is permanently installed on a paper machine. In the preferred embodiment, optical detectors are used to sense the variations occurring in the paper as it is made. Their design facilitates the complex task of classification, allowing local variations to be separated from those that extend across the web.

The signals from these detectors pass through a number of stages of digital processing and analysis, and the disturbances present are then assigned to one of a number of classes. Some of these classes of variation can be readily distinguished by the patterns of variation that they cause in the paper web (see the examples illustrated in FIG. 1).

The results from the monitoring system preferably take the form of tables in which the faults currently present in the paper are listed by category together with details of their frequency and intensity. Graphs showing how particular types of variation have changed with time can be prepared from archived results and plotted to order.

In order to facilitate the precise location of the sources of disturbance, some embodiments of the invention incorporate transducers which can be connected to suspected sources of disturbance on the paper making machine (or on the equivalent machine where the web is not of paper). In these embodiments, means are provided to compare the outputs of the transducers on the machine with the sensors on the web, so that the identity or possible identity of the two signals can be statistically tested.

The preferred embodiment of the web monitor system of the present invention is capable of measuring not only the intensity of variation caused by flocs but also their size and size distribution.

The preferred embodiment is also capable of detecting and measuring unstable machine direction streaks. These have not previously been measured by an on-machine device, although they have been studied in laboratories. The preferred embodiment of the present invention can separate them rather easily from other disturbances. Such streaks contribute significantly to the look-through of paper seen against the light, and they are therefore of commercial if not of practical significance.

The preferred embodiment can also detect macroforming faults, periodic variations caused by mechanical faults and slow, often random variations in the consistency of the dilute pulp from which the paper web is formed. It is also capable of detecting temporary increases of variation caused by intermittent faults with durations from less than 0.01 second up to 30 seconds or more. The events can be classified by frequency and duration, and either logged in a two-way table or individually time stamped and saved in the form of time tracers for subsequence examination.

The preferred embodiment concentrates particularly on detecting basis weight variation, but is also capable of detecting and distinguishing press-roll vibration from calender stack vibration. Both of these cause thickness rather than weight variations.

In the preferred embodiment, and in contrast to some prior art systems, the monitor does not scan the web in the cross direction. Instead, there are a plurality of detectors which are stationary and which are spaced across the web in the cross direction.

Preferably, the system classifies faults by their cross direction width, and either by their machine direction duration or by their frequency. It also classifies according to whether they occur continuously or intermittently. The system then preferably includes means for suggesting the probable location of the cause, thus providing the engineers with the information that they need to locate it accurately. Means may be provided for comparing the suspected source with the variation in the web, and for calculating the probability that the cause has been correctly identified.

Preferably, the system includes means for determining whether the source of the variation measured in the paper web is on the paper machine itself, or whether it is caused by auxiliary equipment. Means for determining the probable rotation speed of the mechanical component responsible may also be provided.

When calculating additive or subtractive combinations of the raw signals, an interleaving method is preferably used. Preferably, the signals from a first plurality of detectors are summed, and the signals from a second plurality of detectors are also summed. The first plurality is interleaved with the second plurality in the cross direction. Then, the signal representative of the sum of the first plurality may be subtracted from the signal representative of the sum of the second plurality.

In one preferred embodiment there may be a first plurality of detectors which are adjacent to the front side of the web, and a second plurality which are adjacent to the back side.

The invention may be carried in to practice in a number of ways and several specific embodiments, and variations on those embodiments, will now be described by way of example with reference to the accompanying drawings, in which:

FIG. 3b is a side elevation of the lookers of FIG. 3a;

FIG. 4 illustrates various fibre optic combinations;

FIG. 5 shows an alternative embodiment of the lookers of FIGS. 3a and 3b;

FIG. 6 shows how the looker modules of FIG. 5 can be positioned across the web;

FIG. 7 shows possible DSP multiplexed inputs;

FIG. 2 shows, very schematically, the main features of a web monitoring system according to a preferred embodiment of the present invention. In the drawing, the paper machine is indicated schematically by the dotted line 2.

The system itself consists of two or more lookers 6, 8, one of which is located over the front side and one over the back side of the paper web 4 near the end of the drier section (not shown). Signals from the lookers are fed to a cabinet 10 close to the machine 2 which contains a power supply for the lookers, a PC board (PC1), and a digital signal processing (DSP) board. PC1 communicates with a further PC 12 (PC2), located in the machine control room which is schematically indicated by the dotted lines 14. PC2 serves as an operator console.

PC1 has, in addition, facilities to take in signals corresponding to variations from suspected sources of disturbance at the wet end or elsewhere on the machine, as an aid to diagnosis. These signals are derived from portable transducers (not shown).

The lookers 6,8 convert variations of reflectance or opacity to optical signals that are transmitted to the cabinet 10. Here they are converted to electrical signals which are sampled by the DSP board. The use of two lookers allows variations extending the full width of the web to be distinguished from local variations. The lookers each input a similar area of the web.

The computer PC1 supervises and controls the activities of the lookers and the DSP board, under the direction of PC2 12. In particular, it selects two or four optical signals to be read by the DSP board, and down-loads to the DSP board the code used for their analysis.

The DSP board checks the validity of the looker signals, then carries out the preliminary analysis. Typically, two signals are sampled for a period of about 30 minutes. Large numbers of FFTs (Fast Fourier Transforms) are calculated. At the end of the sampling period the FFTs are averaged, further processed by PC1, and sent to PC2.

The computer PC2 12 completes the analysis of the data from PC1, and outputs the results to a VDU or printer (not shown). It accepts instructions from the operator about the type of analysis that is required, and sends appropriate instructions to PC1. Also it is responsible for archiving the results on hard disk and for preparing summaries of past results. Computer PC2 may host an expert system to help operators locate sources of disturbance.

Figure 1:
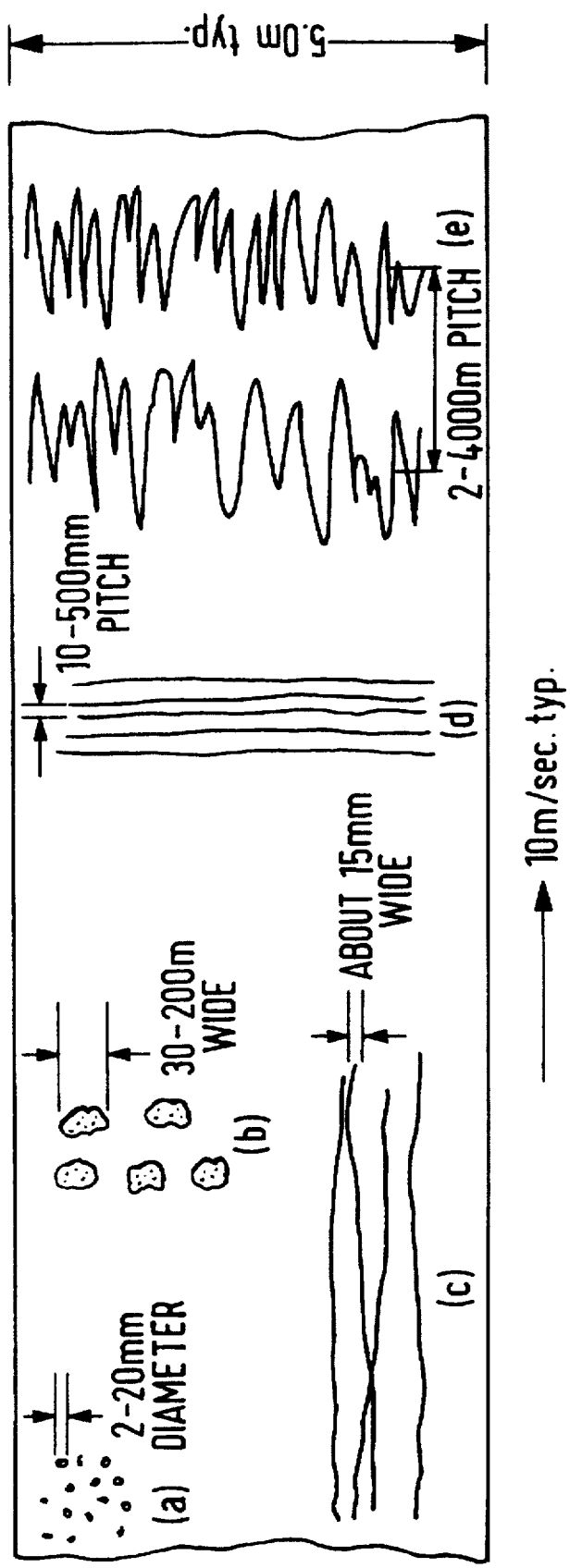
FIG. 1 illustrates examples of patterns of variation that can occur in paper webs.
Figure 3B:
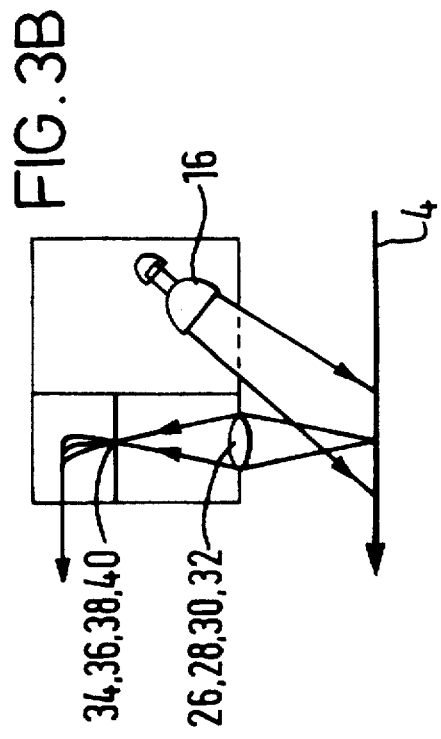
Figure 3A:
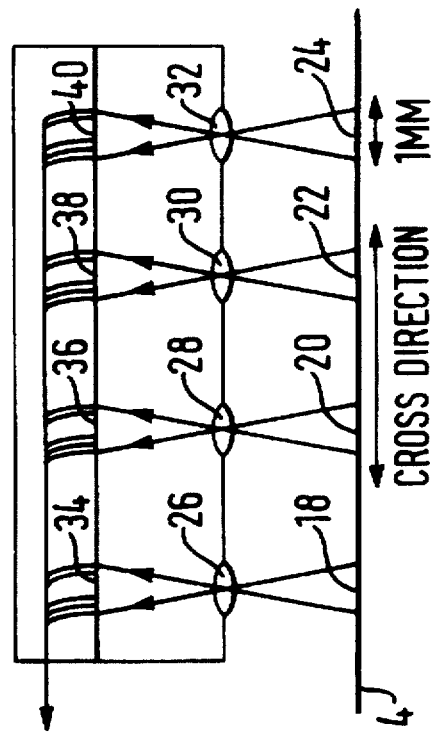
FIG. 3a is a front elevation of one embodiment of suitable lookers that can be used with the system of FIG. 2.

The exact design of the lookers 6,8 is to some extent arbitrary: all that is required is a design which will allow detection of variations in light transmitted or reflected by the moving paper web. One specific exemplary embodiment (not currently the preferred embodiment) is illustrated in FIGS. 3a and 3b. The lookers may be sensitive to any appropriate characteristic of the web, such as moisture content or colour. In an alternative embodiment (not shown) the lookers may be replaced with devices for measuring the electrical conductivity of the web, for example by the use of contact pads.

The basic principle in the preferred embodiment is to illuminate brightly an area of the web and focus its image on the ends of fibre optics arranged in a long row across the web, (and therefore perpendicular to the direction of motion of the paper web). The light from bunches of these fibre optics is directed onto photodetectors (preferably photodiodes) (not shown) to obtain electrical signals corresponding to the variations in the paper web. These photodetectors are housed in the cabinet 10 at the backside of the machine 2 in a temperature controlled environment.

The area viewed by each fibre optic is 0.8–1.3 mm diameter, so that small scale variations can be detected if necessary. The paper web moves at about 10,000 mm/second; the looker signals must be sampled at about 10 kHz to record such small scale variation. The overall width of web that can be viewed by each looker is about 260 mm. To allow variations extending across the full width of the web be distinguished, two lookers are installed, one near each edge of the paper.

As will be seen from FIGS. 3a and 3b, the internal construction of the lookers is modular. Four lamps 16, arranged in a row, illuminate four separate areas of the web 18,20,22,24. Each area is viewed by one of four simple lenses 26,28,30,32 that focuses an image of part of the web area onto a group of fibre optics 34,36,38,40. The arrangement of the optical fibres in each group is similar. Each group is arranged in a row and the individual rows are aligned so they form the single long row referred to above.

By collecting the light from bundles of fibres, the output of a photodiode can be made to correspond to the sum of the variations at number of points. FIGS. 4A to 4D show examples of bundles formed using fibres from different groups. By taking the differences between photodiode outputs corresponding to the pairs of bundles shown here, it is possible to reduce or eliminate contributions from variations extending across the web. Thus signals can be obtained that correspond mainly to:

(1) Periodic and low frequency variations: FIG. 4A
(2) Flocs and streaks only: FIG. 4B
(3) Flocs, streaks and macro forming faults: FIGS. 4C and 4D.

This facilitates further processing.

The spacing d of the pairs of fibres shown in FIG. 4A should be chosen to be wider than the flocs and streaks to be detected. A range of spacings can be provided by adding further bundles of fibres. (Three bundles give 2+1=3 possible spacings, while five give 4+3+2+1=10).

To determine an appropriate value of d, an initial test should be carried out. The value of d should initially be chosen to be small, and it should gradually be increased until the coherence between the signals from the two bundles selected falls to a low steady value.

An attraction of the above arrangement is that the light from any given inspection area could be directed to a number of photodiodes, according to the inspection area groupings required. However, the complexity of this arrangement increases rapidly as further groupings, even for the same few inspection areas, are added. Accordingly, the arrangement shown in FIGS. 3A and 3B is presently not preferred.

In the preferred scheme (FIG. 5) the numbers of inspection areas are limited to two per looker module, except when a measure of floc or streak width is required. The looker modules are restricted to two or four across the width of the paper web. With this arrangement it is feasible to use one dedicated photodiode with its own fibre optic bundle for each inspection area. Although this makes the separation of different patterns of variation in the paper web less sharp, it leads to considerable simplification both of the monitoring system and the subsequent DSP calculations. It also has the advantage that the signals from each area can if necessary be individually corrected for the non-linearity of the relationship between basis weight and optical signal. The ideal looker would be designed to take into account the particular patterns of variation in the web for which it was intended, and to give sharp separations or patterns having different CD widths. However, since the characteristics for the patterns are not accurately known in advance and may change with time, it is preferable to chose a general purpose looker design that can readily be modified. The preferred system can be specified very simply by the spacing of the pairs of inspection areas seen by each module, together with the spacing of the looker modules.

FIG. 5 shows two views of a basic module designed to observe reflectance variation at two small areas 42,44 of the web 4. The web is illuminated in this case by means of a remote light source (not shown) and fibre optic light guide 46. The light collected from each inspection area is conducted by further small light guides 48,50 to remotely sited photodiodes. In some cases the web 4 might be illuminated from below in order to sense variations in light transmission. It will be noted that each light guide leads to a separate photo detector. This provides an electrical signal which may then be sent by multiplexers (FIG. 7) to one of four delta-sigma converters at the input to a DSP board. The DSP board may then be used to add or subtract the signals before they are further analysed.

FIG. 6 shows four of the modules illustrated in FIG. 5, designated with reference numerals 52, 54, 56, 58, arranged across a paper web 4, two near the FS and two near the BS. Each module 52, 54, 56, 58 outputs two optical signals designated A or B to a group of multiplexers 53, 55, 57, 59 feeding the DSP system analogue to digital converters (see FIG. 7). In this embodiment the multiplexer 53 receives signals from the lookers 54, 58; and the other multiplexers likewise receive signals from two separate lookers. In the general case, the multiplexers could also accept signals from other measuring stations along the length of the paper machine.

The multiplexer combinations shown in FIG. 7 gives the DSP system access to all necessary input combinations. To give some examples:

(i) Signals 1A and 1B may be added or subtracted and the result compared with a sum or difference of 3A and 3B. The differences (1A−1B) and (3A−3B) gives two independent measures of floc and streak intensity at the BS of the machine, the effects other CD variations being eliminated. At the same time, the signal corresponding to (1A+1B−3A−3B) gives a measure of the intensities of macroforming faults extending between lookers 1 and 3 at the BS of the web, with CD barring eliminated but with some contribution from flocs and streaks.

(ii) Similarly, the signals 2A, 2B, 4A and 4B may be compared to obtain information about the similar variations at the FS of the machine.

(iii) Signals 1A, 2A, 3A 4A, may be combined and compared. For example two channel spectral analysis of the sums (1A+3A) and (2A+4A) allows the variations extending across the full width of the paper web to be distinguished from those that extend less far, even if there are phase lags between the variations affecting the FS and BS of the web.

Figure 8:
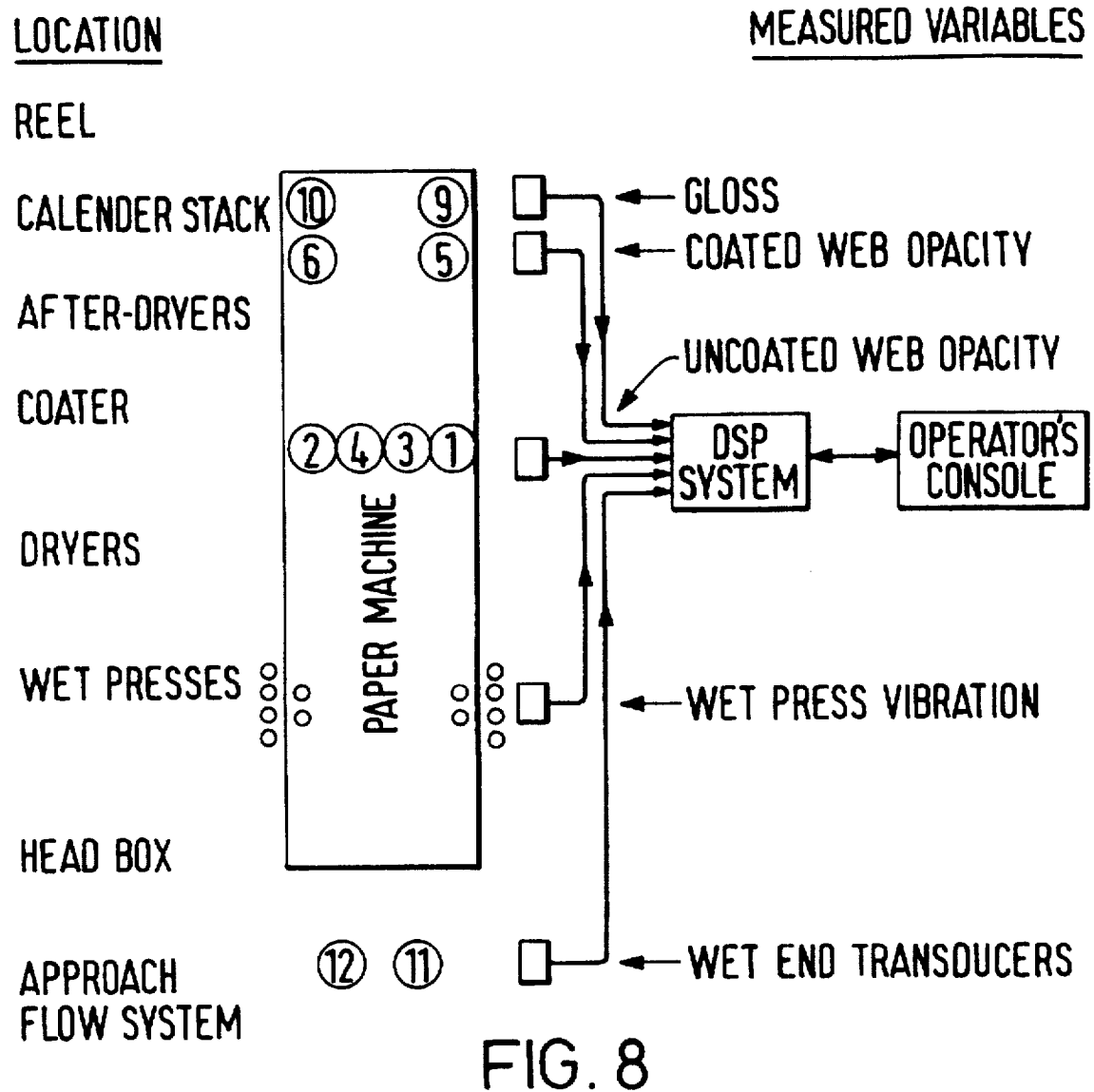
FIG. 8 shows possible measuring stations for a large monitoring system.

FIG. 8 shows a possible arrangement of lookers and other transducers throughout a paper machine. Such an arrangement can be built around a single 4-input DSP board fed by 8-way multiplexers. Some local multiplexers are also needed where there are several transducers at one measuring station. It might also be helpful to duplicate the DSP board and its multiplexers, but neither amendment causes undue difficulty.

In this form a monitoring system would be able constantly to examine the variations in the paper as it is made and to identify many individual sources of variation. The addition of a gloss monitoring station allows thickness and roughness variations, often caused by wet press vibration, to be sensed. The monitoring of press rotation would allow the causes of such roughness variation to be pinpointed. The combination of gloss and wet press monitoring allows sound judgements to be made on the wet press faults presents Preferably, the press roll and press felt rotations should be used to generate trigger signals (one pulse per rotation). Signal averaging or dual channel spectral analysis may then be used to determine the contribution of each rotating element to the variation of gloss or, if appropriate, the vibration that can be observed by transducers mounted on the press roll bearings.

Wet end transducers can be added, temporarily or permanently, to allow comparisons of variations in the approach flow system with those in the paper, thus confirming the conclusions reached by examining the data from the web monitoring stations. They are not seen as an essential part of the system.

As has previously been indicated, the lookers may be positioned to receive signals from any required areas of the moving paper web. Typically, the lookers will be placed in a line, across the paper web, although that is not essential. In some embodiments (as discussed further below) it may be desirable to use a rectangular group of looker modules. It is of course obvious that signals from two inspection areas which are aligned in the machine direction will give rise to signals which come from the same area of the web, but with a time delay between them. If use can be made of that fact, then a single CD row of inspection areas can provide all the necessary information: this can be achieved by means of a multiplexer and DSP board, as previously discussed. Nevertheless, it may sometimes be convenient to use a rectangular arrangement of four inspection areas, since this allows the separation and direct measurement of flocculation from other patterns of variation by rather simple means.

A discussion of the way in which various patterns can be detected by different combinations of inspection areas will now be presented.

The separation of patterns is brought about in two stages. Firstly, by adding or subtracting the signals from suitably selected inspection areas, resultant signals are obtained in which the effects of certain patterns or variation are either diminished or totally eliminated. For example the difference between the signals from two areas one inch (2.5 cm) apart in the cross direction will not be affected by barring that extends uniformly across the web. In the second step, the power spectra of these manipulated signals are calculated and subtracted one from another, with the application of suitable weighting, to obtain estimates of power spectra of individual patterns of variation.

It will be appreciated that in the embodiment of FIGS. 3A and 3B, the first step is at least partly achieved by optically summing the signals from different inspection areas 18, 20, 22, 24 using groups of optical fibres. In the other embodiment of FIG. 5, where each inspection area produces its own signal, both the first step and the second step are carried out digitally.

Clearly, this method works only if the patterns in the web differ significantly in at least one dimension. It depends on some prior knowledge of the nature and typical dimensions of such patterns to be expected in the web. On the whole they are similar in all paper machines, but if necessary can be checktheso that suitable spacings of the inspection areas can be selected. This is within the capability of a person skilled in the art.

This approach is particularly valuable for the separation of patterns that differ in their cross direction dimension. Such patterns cannot be separated by analysis of the variations seen at only one fixed point across the machine.

The separation of patterns by use of lookers is dependent on the assumption that certain patterns, such as barring, are strictly aligned with the cross direction. While this is so for CD distances of 300 mm or so, it may not be so for the full 5000 mm width of a typical paper machine. To deal with this difficulty, dual channel spectral analysis must be used. The CD widths of lookers are desirably therefore restricted to 300 mm or so.

To separate faults in the web according to their CD width, it is sufficient to observe the web at only two points separated by this width. The signals from the two areas will be coherent for wider faults. Narrower features, randomly disrupted over the web, will not lead to coherence between the two areas. To be more precise, the observed coherence will depend on the cross-correlation function of this random distribution of features. This must fall to zero when the observation points are separated by more than the feature width.

The value of using more than two observation areas in the CD has yet to be explored. It is probably capable of enhancing the separation of patterns of rather similar CD width, and it should give better estimation of flocculation intensity should this tend to vary across the machine. However, these improvements would be at the cost of increasing complexity.

Before they can be analysed, signals representing variations on a paper machine must first be filtered (smoothed) in order to remove irrelevant high frequencies that would otherwise cause "aliasing" and thus confuse the subsequent analysis. The filtered signals may then be sampled (digitised) to obtain a sequence of values, known as a "time series", suitable for analysis by a computer.

In the case of signals representing the non-uniformity of the paper web, sampling may be carried out either at constant distances along the moving web or at constant increments of time. This choice depends on whether the speed of the paper machine varies appreciably with time and if so, on whether the variations to be studied are thought to be caused by faults in the machine itself rather than in off-machine equipment.

Because the looker is a key component of the system, it is now proposed to consider the design and the underlying theory in more detail with particular reference to the separation of the different patterns of variation expected to occur in the paper web.

The function of a looker is to produce output signals corresponding to variation present in the moving paper web. By careful choice of the parts of the web seen by the looker, its response to different patterns may be varied. Sequences of output signals can thus be provided that correspond to the effects of, for example:

(1) Flocculation only
(2) Flocculation and unstable streaks
(3) Flocculation, unstable steaks and macro forming faults
(4) Flocculation, streaks, macro forming faults and barring, where "barring" is a term used to refer to any pattern of bands of variation extending uniformly across the web. Such signals do not respond identically to individual defects in the web, and so cannot be subtracted to yield the signals corresponding to individual causes of variation. Their statistical properties and their power spectra do however correspond and they can be subtracted to obtain the characteristics of individual types of variation. (To avoid confusion it should be mentioned that the patterns referred to do not include small-scale wire mark and suction roll patterns for which a different approach is necessary.)

Figure 9:
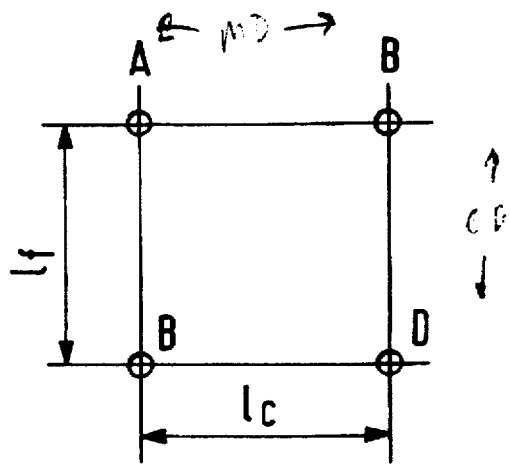
FIG. 9 shows four exemplary inspection areas.
Figure 10:
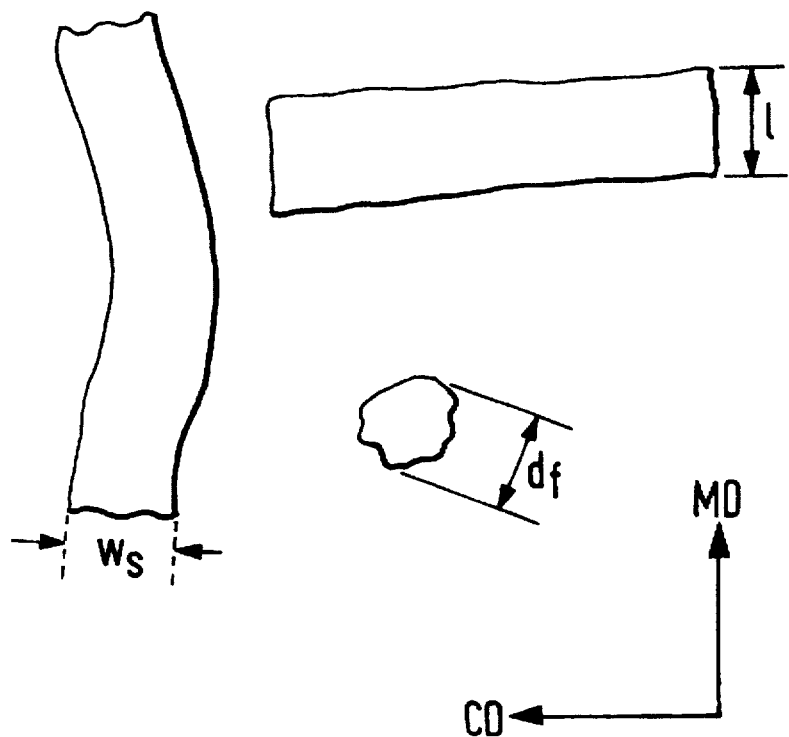
FIG. 10 shows various patterns of variation in the paper web that can be recognised using the inspection areas of FIG. 9.

This approach will now be illustrated by a hypothetical example. FIG. 9 shows four inspection areas, lettered A-D, arranged in a rectangle with its sides aligned with the machine and cross directions (the MD and CD) of the web. FIG. 10 shows the maximum widths of the flocs, unstable MD streaks, and CD bars present in the paper. The MD length of the rectangle must be is chosen to exceed the width of any bar, the CD width must exceed the width of any streak, and both must exceed the diameter of any floc.

It must also be assumed, for this example only, that the bars are distributed at random in the machine direction and are not caused by a periodic disturbance.

If we take the variable cv to represent the coefficient of variation of the signal that is produced at any individual inspection area, then because the squares of cv's are additive we can write down an equation which indicates how the variation at any single inspection area may be broken down:

$$cv^2(\text{single inspection area}) = cv^2(F) + cv^2(S) + cv^2(P) \quad (1)$$

where $cv^2(F)$, etc refer to flocs, streaks and bars, respectively.

If the variations at two areas A and B, aligned with the machine direction, are summed, the combined $cv^2$ will be:

$$cv^2(A+B) = [cv^2(F)]/2 + cv^2(S) + [cv^2(P)]/2 \quad (2)$$

The relative contribution of the streaks to the total variation is thus increased. In contrast, if the outputs A and B are subtracted, then the $cv^2$ of this difference (still calculated using the mean for the web), will be:

$$cv^2(A-B) = [cv^2(F)]/2 + 0 + [cv^2(P)]/2 \quad (3)$$

Here the unstable streaks, which are assumed to be much longer than the distance between areas A and B, contribute nothing to the $cv^2$ of the difference. Thus the contribution from the streaks alone can in principle be found from:

$$cv^2(\text{unstable streaks}) = cv^2(A+B) - cv^2(A-B) \quad (4)$$

It must be emphasised that this example is only of hypothetical interest. The calculation holds only if the distance "$l_r$", FIG. 9, between areas A and B is greater than the width of any bar and only if the MD spacing of the bars is random. In practice these conditions cannot usually be met.

It is nevertheless possible to obtain a practical signal corresponding solely to flocculation from this simple arrangement of inspection areas, regardless of the spacing of the bars in the machine direction and regardless of their periodicity. The $cv^2$ of the quantity (A−B−C+D) may be obtained by pooling the light from pairs of fibres or otherwise adding the output signals to obtain signals equivalent to (A+D) and (B+C), taking their difference and calculating its coefficient of variation. Because the areas A&C, and also B&D, are equally affected by the bars, while the $cv^2$ is calculated from the differences between these pairs, bars will not contribute to the $cv^2$. Similarly, this $cv^2$ will be unaffected by streaks. It can be shown that:

$$cv^2(\text{flocculation}) = 4 * [cv^2(A-B-C+D)] \quad (5)$$

or $$cv(\text{flocculation}) = 2 * [cv(A-B-C+D)] \quad (6)$$

The variance is divided by four because four independent measures of flocculation are pooled.

By extending the inspection areas in the cross direction it becomes possible not only to help separate all the common patterns of variation but also to obtain better average measures of flocculation and unstable streaks. The latter advantage is subject to the limitation that as the number of areas inspected is increased, so the coefficient of variation of the composite signal that is analysed tends to fall. It is thought that adequate averaging will be obtained by combining 8 or perhaps 12 inspection areas. It also is convenient to cluster the inspection areas into 2, 4 or 6 similar groups to facilitate a modular approach to the physical design. The spacing of the groups also makes it possible to separate macroforming faults from defects that extend further across the web.

Figure 11:
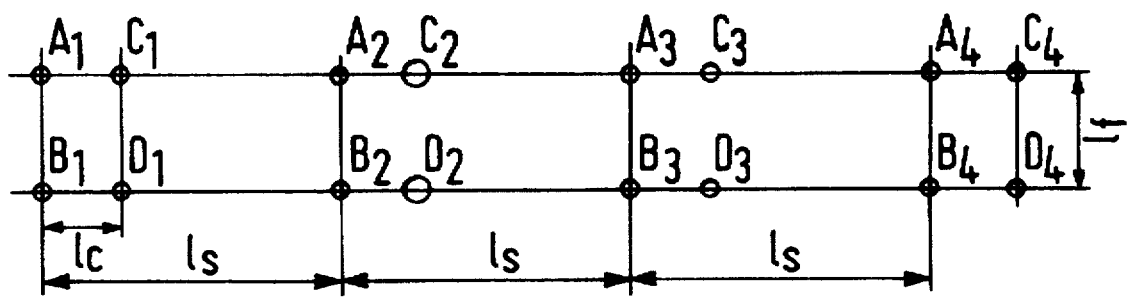
FIGS. 11 to 13 show further possible arrangements of inspection areas.
Figure 12:
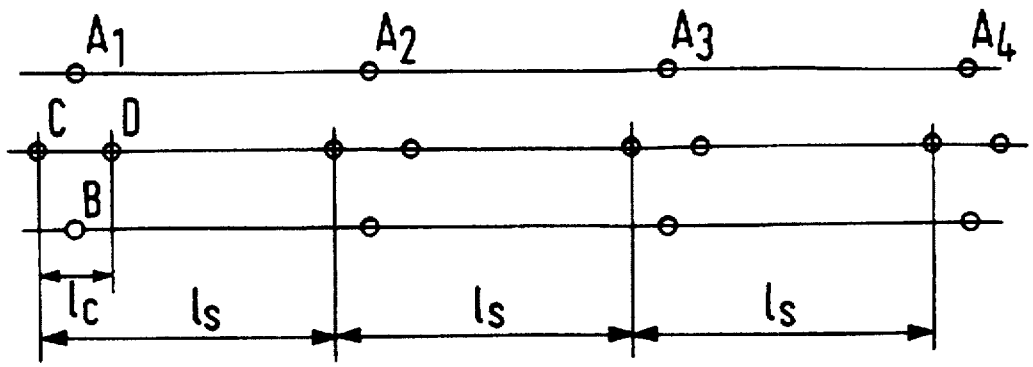
Figure 13:
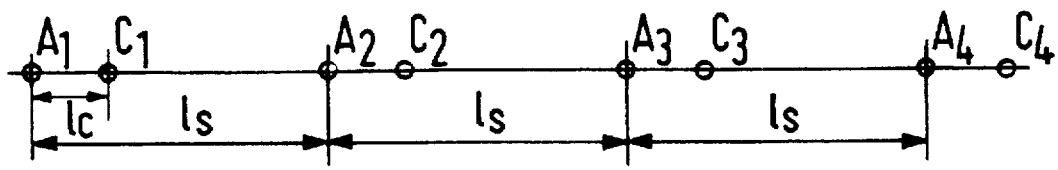

FIGS. 11–13 show three possible arrangements, each using four groups of inspection areas. The locations within groups are lettered, while the groups are numbered. Inspection areas in similar locations in different groups will be distinguished by subscripts. An example of the use of a specific arrangement to separate the main types of variation now follows.

Using the FIG. 11 arrangement, the cv caused by flocculation can be found as follows:

$$cv(\text{flocculation}) = [8^{0.5}] * cv[(A1-B1) - (A2-B2) + (A3-B3) - (A4-B4)] \quad (7)$$

$$cv(\text{flocculation}) = [8^{0.5}] * cv[(A1+B2+A3+B4) - (B1+A2+B3+A4)] \quad (9)$$

The right hand side of the second version of this equation shows how the fibre optics, in the FIG. 3 embodiment, should be bunched together and connected to a pair of photodiodes. The difference of the photodiode outputs is taken and its cv calculated and multiplied by the square root of 8 to obtain the cv contributed by flocculation.

Streaks and flocs cannot be wholly separated. Using the FIG. 11 arrangement, the following is one of four similar equations by which the variance of flocs and streaks together may be calculated.

$$cv^2[(A1-C1)+(A2-C2)+(A3-C3)+(A4-C4)] = \text{var}(\text{streaks})/8 + \text{var}(\text{flocs})/8 \quad (9)$$

$$cv^2[(A1+A2+A3+A4) - (C1+C2+C3+C4)] = \text{var}(\text{streaks})/8 + \text{var}(\text{flocs})/8 \quad (10)$$

Here, the left hand side of the second version shows how, in the FIG. 3 embodiment, the fibre optics are to be routed to a pair of photodiodes. The cv of the difference of the photodiodes outputs is calculated and squared. The variance due to the streaks can then be found from equation (10), using the flocculation variance from equation (8).

The fibre optics bunches used to obtain the cv caused by flocculation may also be used to estimate the variance caused by macroforming faults. With reference to FIG. 11, the sum of their outputs has the following variance:

$$cv[(A1+D1) - (C2+B2) + (A3+D3) - (C4+B4)] = \text{var}(\text{flocs})/8 + \text{var}(\text{streaks})/8 + \text{var}(m'\text{form})/4 \quad (11)$$

Here m'form refers to macroforming faults having CD widths less than the gaps $(l_s-l_c)$ wide, between the four groups of inspection areas. Its variance is found by subtracting from the above result the value found for the left hand side of equation (10).

The variance associated with barring and other similar patterns extending across the web can be found from the sum of the outputs from the fibre optic bunches used to find the variance of the streaks, as follows:

$$cv^2[(A1+A2+A3+A4)+(C1+C2+C3+C4)] = \text{var}(\text{streaks})/8 + \text{var}(\text{flocs})/8 + [\text{var}(m'\text{form})]/4 + [\text{var}(\text{bars})] \quad (12)$$

The variance due to barring is found by subtracting from the above result the value found for the left hand side of equation (11).

It will be evident from this example that a variety of combinations of inspection areas may be used to obtain similar information. It should be noted that the repetition of the rectangular arrangement at different points across the web allows replicate measures of local formation characteristics to be calculated and compared.

The arrangement of FIG. 12 shows an alternative to the above arrangement. The pairs of A and B areas aligned in the MD can be used to measure flocculation and streaks. The areas labelled C and D, all aligned across the machine, could be used to locate macroforming faults and bars. The functionality is similar to that of the above arrangement.

The arrangement of FIG. 13 does not allow a single output to be obtained corresponding solely to the effects of flocculation. It is however a practical arrangement for applications where electronic or digital filtering can be used to separate the high frequency variations caused by flocculation from the lower frequency variations from streaks. The following equations, borrowed from the discussion of the FIG. 11 arrangement indicate how other patterns of variation can be separated by use of the fibre optic bunches suggested in FIG. 3.

With reference to FIG. 4, it will be understood that the sum of the outputs of two fibre optic bunches either in arrangement 4B or 4C gives the following cv:

$$cv^2 [(A1 + A2 + A3 + A4) + (C1 + C2 + C3 + C4)] = \quad (13)$$

$$var(streaks)/8 + var(flocs)/8 + [var(m'form)]/4 + [var(bars)]$$

The difference between the outputs of two fibre optic bunches 4C has the following cv:

$$cv[(A1+C1)-(A2+C2)+(A3+C3)-(A4+C4)]=var(flocs)/8+var(streaks)/8+var(m'form)/4 \quad (14)$$

The difference between the two sets of fibre bunches in 4B has the following components:

$$cv^2[(A1-C1)+(A2-C2)+(A3-C3)+(A4-C4)]=var(streaks)/8+var(flocs)/8 \quad (15)$$

Although the above equations are written in terms of the coefficients of variation that would apply to any given narrow band of frequencies selected from the looker output, they apply equally to power spectra. Power spectra can be calculated either for signals received from one individual inspection area, or more usually from the sum and/or difference of signals from individual areas.

In general, then, power spectra representative of a particular individual pattern of variation may be estimated by:

(a) optically or digitally summing the variations in reflected or transmitted light at a plurality (for example four) observation areas;

(b) Forming new signals from the differences between such composite signals;

(c) Calculating the power spectra of these new signals; and (d) Taking suitably weighted differences between these power spectra.

The appropriate weights depend upon the particular pattern of variation that is being studied; the weights for specific cases may be extracted from the equations such as those given above.

The above process combines two quite different approaches to analysing variations in the paper web. Spatial filtering results when signals emanating from different inspection areas are subtracted one from the other. Two channel spectral analysis comprises comparing the transfer function and coherence between pairs of signals obtained from different inspection areas. Two channel spectral analysis is useful for the separation of variations which extend across the full width of the paper web. These may be caused mainly by faults in the approach flow system, from more localised variations arising mainly at the headbox or in the forming zone (i.e. on the wire). It may also be used for comparison of variations in the web with random disturbances at the wet end of the machine. For this purpose a digital time delay is used to correct for the distance-velocity lag of the paper web.

Figure 14:
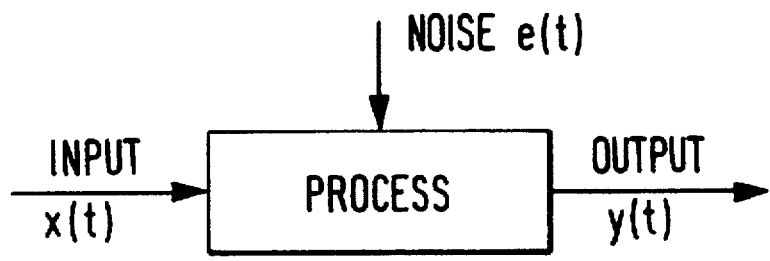
FIG. 14 is a model illustrating the transfer function.

Two channel spectral analysis is commonly used by control engineers to compare the noise-contaminated output "y" of some process with a supposedly noise free input "x", see FIG. 14. It is thus possible to deduce the transfer function of such a process, obtaining attenuation, phase shift and also coherence as functions of frequency. The model underlying the transfer function is also similar to the linear regression model; in both cases is it assumed that "x" is error free.

Figure 15:
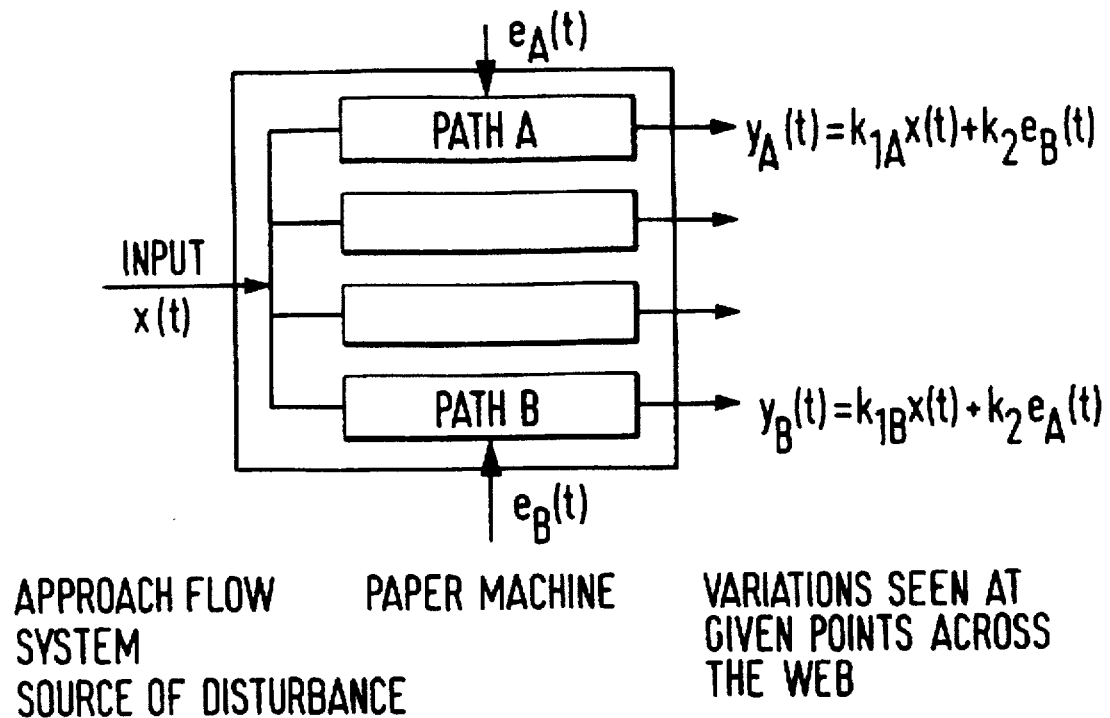
FIG. 15 is a model corresponding to that of FIG. 14, but for a paper machine.
Figure 16:
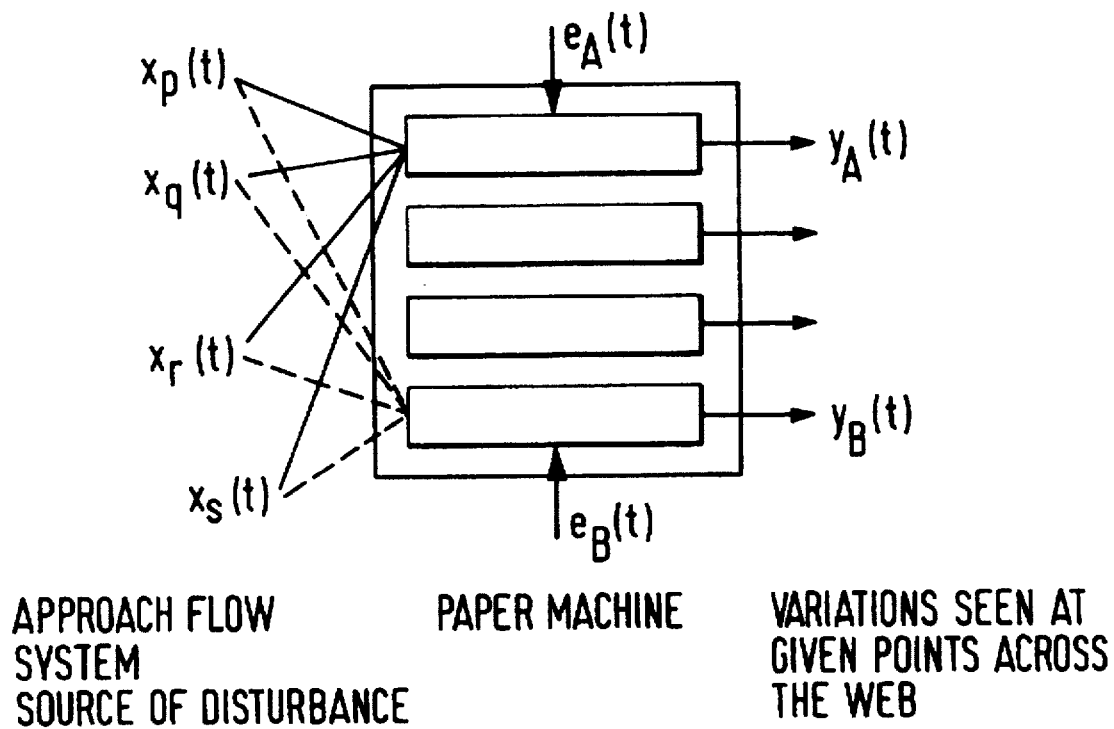
FIG. 16 is a more detailed model corresponding to the model of FIG. 15.

Signals derived from two given points across the paper web will be similarly affected by variations in the approach flow system, but will be independently affected by local variations from the headbox and forming zone, see FIG. 15. It is not possible to obtain a noise free signal corresponding to the wet end variations affecting the paper web (FIG. 16). It is however possible to use the coherence between two signals $y_A(t)$ and $y_B(t)$ corresponding to variations sensed in the web at different cross machine positions to compute power spectra corresponding to (a) the correlated parts of the signals derived from wet end disturbances, and (b) the independent components of variation corresponding to variation associated with the forming process.

FIG. 15 shows a model corresponding to the manufacture of the paper web. The input x(t) affects all parts of the web to a similar extent except that the time lag to different observation points across the width of the web may differ. The complex constants $k_{1A}$ and $k_{1B}$ thus imply similar attenuations at observation points A and B, but differing phase shifts. The added noise signals $e_A(t)$ and $e_B(t)$ affecting the two outputs $y_A$ and $y_B$ have similar statistical properties. Each corresponds to a noise contaminated version of the unknown input x(t). Given $y_A$ and $y_B$, the problem, which can be solved by two channel spectral analysis, is how to distinguish the systematic variation corresponding to x(t) from the noise.

The paper web is affected by two types of variation:

1. Variations such as head box vibration, or thin stock consistency variation, which affect the full width of the web and therefore cause correlation between the variations detected at, say, the FS and BS.

2. Variations caused by localised faults such as individual flocs or unstable streaks which, being randomly distributed throughout the web, affect the FS and BS independently.

Coherence can be used numerically to separate the variations in the FS and BS spectra into spectra of "correlated" and "uncorrelated" parts, corresponding to the above two categories.

FIG. 16 shows a more realistic representation of a paper machine system than FIG. 15. There are many possible sources of disturbance at the wet end which tend to arrive at different parts of the paper web by differing routes and thus with differing phase lags. It is not possible to obtain any single measure from the wet end that fully represents the inputs to different points across the width of the machine.

Although periodic variations can readily be recognised and located as spikes in well averaged power spectra, the background variation on which they are superimposed must be independently analysed. A method for removing these spikes so as to leave the background free for further analysis has been developed. It is essentially an iterative method. A general purpose curve is fitted to the spectrum and the spikes deviating widely from this curve are recognised and replaced by interpolated values from the existing background. The process is repeated until no further spikes are found.

Once a despiked background has been obtained, it is possible to fit suitable bell shaped curves to broader humps with known causes. For example, if spectral density has been plotted as power per octave vs the logarithm of frequency, the humps caused by flocculation and by unstable streaks can be distinguished, fitted with Gauss function related curves, and thus the intensities and machine direction dimensions can be determined.

Periodic variations can be classified dependent on whether or not they vary in frequency as the speed of the paper machine is changed. Also, harmonically related frequencies, probably all caused by the same fault, can be grouped together.

Further details will now be given of the way in which the spectra and the spectral functions are calculated.

In order to obtain an adequate digital representation of an analog signal, the digital samples (readings) of that signal must be taken at a frequency that is at least twice the highest frequency present in the analog signals. If any variations with frequencies higher than twice the sample rate are present they must be filtered out before the signals are sampled to avoid misleading results (caused by "aliasing").

Usually two analog signals are sampled simultaneously, each at a sampling rate of, say 8192 Hz. Blocks of 1024 successive samples per signal are accumulated in a buffer, then checked and used for subsequent calculations. Later, to provide increased resolution, blocks of up to 8192 samples may be used.

In order to study low frequency variations, further blocks of data are required that have been sampled at lower frequency. A block of 1024 values may be "decimated" to give 512 values corresponding to half the original sample rate. During decimation, high frequencies that would cause aliasing are removed by digital filtering. After filtering, alternate samples may be omitted without further loss of information. Two blocks of data are therefore used to produce one block of the same length but half the original sample frequency.

In the web monitor code the sampled data are decimated repeatedly to provide data for the calculation of spectra over ten or more frequency ranges.

There is an extensive literature on the Fourier transform; only the essentials are mentioned here. This transform may be computed by an algorithm known as the Fast Fourier Transform, (FFT). If an FFT is performed on a sampled signal of 1024 (real) values, it yields 512 complex values in the form of 512 real (cosine) parts and 512 imaginary (sine) parts. This complex spectrum covers the frequency range zero to half the sampling frequency. Each of the 512 complex values is said to occupy a separate "bin". Ideally, each bin contains components lying solely within a frequency band of width equal to $1/1024$th of the sampling frequency. In the analysis of practical data the energy from each component is spread over a number of bins. Such "leakage" is usually controlled by the weighting of the blocks of data and also by adjusting the block means to zero before calculating the transforms.

Rather than plot the real and imaginary parts, Re(f) and Im(f) of a complex spectrum, it is preferable to combine them to obtain the power S(f) or amplitude Am(f) and then plot these as power or amplitude spectra. Note that $$S(f)=[Re(f)]^2+[Im(f)]^2 \quad (16)$$
$$Am(f)=[S(f)]^{0.5}$$

If two signals, A and B, are sampled in synchronism, and FFTs of the two corresponding data blocks are calculated, then the phase information implicit in the transforms may be used to calculate the relative phase of the contents of each bin. The first step is to calculate the power and cross spectra.

$$SA(f)=[ReA(f)]^2+[ImA(f)]^2 \quad (18)$$
$$SB(f)=[ReB(f)]^2+[ImB(f)]^2 \quad (19)$$
$$PAB(f)=ReA(f)*ReB(f)+ImA(f)*ImB(f) \quad (20)$$
$$QAB(f)=ReA(f)*ImB(f)-ImA(f)*ReB(f) \quad (21)$$

The cross power spectra, P(f) and Q(f) for short, are vectorial components containing phase as well as amplitude information. It follows from the above equations that $$[PAB(f)]^2+[QAB(f)]^2=[SA(f)]*[SB(f)] \quad (22)$$

The relative phase angle Pha(f) may be calculated for each component from the following equation.

$$\tan [PhaAB(f)]=[QAB(f)]/[PAB(f)] \quad (23)$$

Before going further, a model will be suggested for a pair of signals, yA(t) and YB(t) obtained from transducers at two points on a paper machine. Suppose that both signals are affected by disturbances x(t) from some common source at the wet end. In addition, suppose Signal A is also affected by the variations eA(t), while B is independently affected by the variations eB(t). Each signal may be a random, narrow band, or periodic variation, or a mixture of these.

The common variation x(t) may take differing times TA and TB to arrive at the transducers from which yA(t) and yB(t) are obtained. Also, each variation may suffer attenuation to a varying degree. The signals may thus be represented by $$yA(t)=A1.x(t-TA)+A2.eA(t) \quad (24)$$
$$yB(t)=B1.x(t-TB)+B2.eB(t) \quad (25)$$

If the paper machine system is stable, the coefficients A1, A2, B1 and B2 and also the lags TA and TB will be constant. If all sources of disturbance have steady mean amplitudes, then the characteristics of yA(t) and yB(t) will be steady.

Individual power spectra simultaneously calculated from signals yA(t) and yB(t) will exhibit sharp peaks if relatively strong periodics are present in the variations, but their backgrounds, associated with random variations, will be irregular. To obtain more useful information, individual spectra must be averaged.

Power is an additive quantity. Power spectra from the repeated sampling and FFT calculations on many blocks of date may be summed, term by term, then divided by the number of sums, N, to get the averaged power spectra. In order to obtain reliable spectra to be used in the study of random variations it is essential either to average the individual spectra or to smooth them to remove the statistical variations caused by random disturbances.

This averaging process may also be applied to the cross power spectra. With reference to the previous section, averaging removes from the cross products the contributions of the uncorrelated components eA(t) and eB(t), leaving only the effects of the common component x(t). It follows that, provided the common component is not extremely small in the original signals, its relative phase can now be reliably calculated for each bin using equation (23).

The spectral function known as coherence may also be calculated from the averaged power and cross spectra. As the averaging proceeds, so the contributions of unrelated components of cross power spectra decay so the equality give in equation (22) no longer holds. This suggests that, for well averaged spectra, it should be possible to use the cross spectra to estimate the contributions to the power spectra of the common components. Coherence provides such an estimate. It is calculated as follows from the ratio of the left and right hand sides of equation (22).

$$CohAB(f) = \frac{[\Sigma PAB(f)]^2 + [\Sigma QAB(f)]^2}{[\Sigma SA(f)] * [\Sigma SB(f)]} \quad (26)$$

The symbol $\Sigma$ indicates a summation. Coherence is normally represented by gamma squared. It is function of frequency, and thus may be calculated for each bin for a set of averaged spectra. Otherwise it is similar to $r^2$, the square of correlation coefficient.

Suppose that variations caused by the approach flow system and by forming faults are superimposed in the paper web, and are observed by means of lookers placed near the FS and BS edges of the paper web. Assume that all variations are measured in the same units, and that all point across the paper web respond similarly to the sources of disturbance. This is equivalent to putting all the coefficients in equations in equations (24) and (25) equal to one. The time lags TA and Tb may differ, so that the looker signals correspond to x(t–TA) and x(t–TB).

Suppose that variation of the second type is caused by small randomly distributed defects that individually affect only a small part of the width of the web. Such variations would cause signals from the FS and BS lookers to vary independently with var(e). Denote these signals by eA(t) and eB(t).

When the two effects were superimposed, the signals yA(t) and yB(t) output by the lookers would be $$yA(t)=x(t-TA)+eA(t) \quad (27)$$

$$yB(t)=x(t-TB)+eB(t) \quad (28)$$

Each signal would have similar variance $$var(yA)=var(yB)=var(x)+var(e) \quad (29)$$

If a suitable correction could be made for the time lag, the covariance would be given by $$cov(yA,yB)=var(x) \quad (30)$$

Because the method of calculating coherence gives a result that is unaffected by time lag, so long as it is constant, the relationship between coherence and variance is as follows.

$$[cov(yA,yB)]^2=coherence*var(yA)*var(yB) \quad (31)$$

In practical cases the variations seen at FS and BS of the machine will not be equal, the quantity $$var(y)=[var(yA)*var(yB)]^{0.5} \quad (32)$$

may be regarded as pooled mean variance at FS and BS It follows from equations (30) and (31) that:

$$var(x)=[coherence]^{0.5}*var(y) \quad$$

The square root of coherence therefore gives the proportion of the variance of the signals (or of their power, in spectral analysis terms) that is caused by variations from the approach flow system. The proportion of the variance caused by localised forming faults is the complement, [1–coherence$^{0.5}$].

Figure 2:
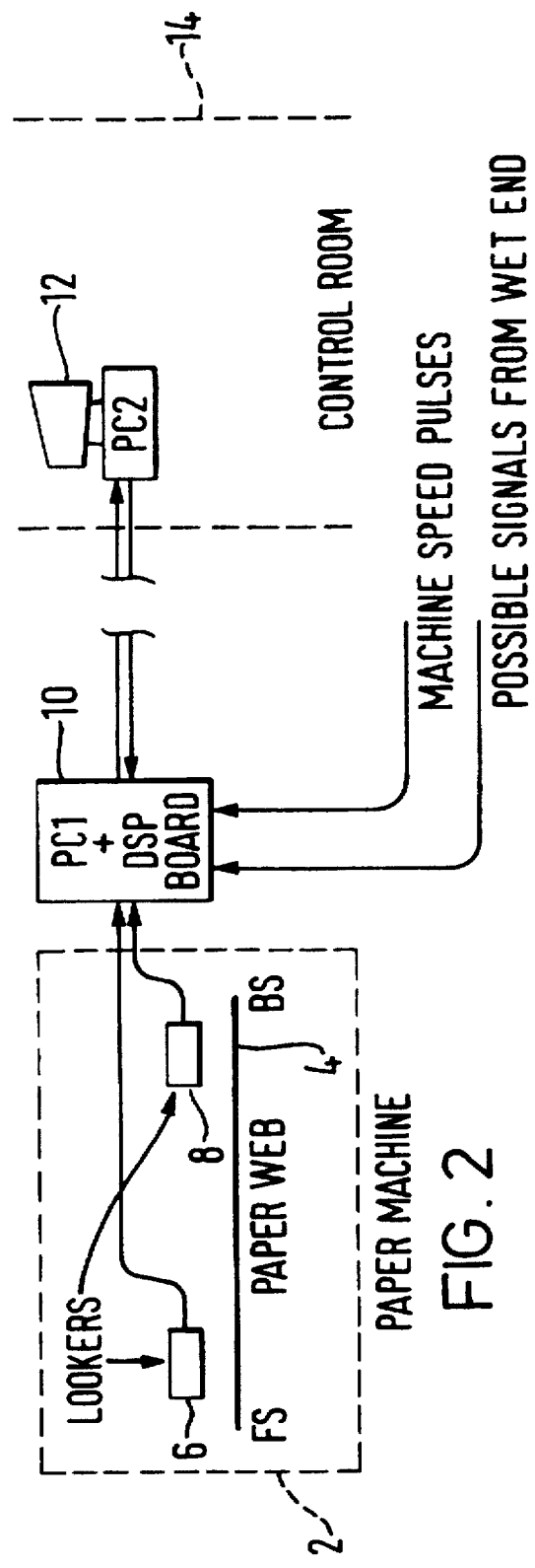
FIG. 2 shows the components of a web monitoring system embodying the present invention.

In a practical working embodiment the above signal processing tasks will normally be jointly executed by PC1 and the DSP (FIG. 2). The practical tasks to be carried out by the system are set out below:

(A) Set up and test signals from the lookers, and analyse time traces.

(B) Computer FFTs simultaneously over ten or more octaves of frequency, as follows:
   (1) Continuously sample, check and scale two signals, or in some cases, two pairs of signals. In the latter case, compute the difference of each pair of samples and use this for the subsequent calculations.
   (2) Repeatedly decimate the sampled data to obtain new data at one half, one quarter, etc., down to 1/512th or so of the original sampling rate.
   (3) Compute FFTs of blocks of the original and of the decimated data as it becomes available, to obtain "complex" spectra.
   (4) Either
      (a) compute and analyse individual spectra to detect abnormal variations (Event capture), or
      (b) calculate and accumulate sums of power and cross spectra for later calculation of averaged spectra (including phase and coherence).

(C) Analyse the averaged spectra generated by (B), as follows:
   (1) Calculate and list the total power over each octave band.
   (2) Locate "spikes" caused by periodic variations.
   (3) For selected spectra, separate the spikes from the background and save both.
   (4) For spikes from the FS and BS of the machine:
      (a) Form a list of significant periodics and their amplitudes,
      (b) Classify these periodics according to the fundamental frequencies of their supposed causes.
   (5) For the backgrounds of selected spectra, combine the results for each octave range to obtain a plot of power per octave against the logarithm of frequency.
   (6) For the background to spectra of flocculation and streaks:
      (a) Locate the two main maxima.
      (b) Fit curves to the corresponding humps to determine the intensities and machine direction lengths of the flocs and streaks.
   (7) For the background to the spectra of microforming faults:
      (a) Remove the contributions of the flocs and streaks.
      (b) Calculate the intensity and machine direction length of the macroforming faults.
   (8) For the background to the correlated parts of the signals from FS and BS of the machine:
      (a) Search for "humps" corresponding to sources of narrow band disturbance affecting the full width of the machine.
      (b) Determine the intensity and mean frequency of each suppose disturbance.
   (9) For the background to the uncorrelated parts of the FS and BS signals, calculate its total intensity and if of practical significance determine its characteristics.

(D) Compare signals from the web with signals from the wet end, etc. The signals from the wet end must be delayed to correct for the time taken by the paper to reach the lookers. This lag must be carefully adjusted to maximise the correlation of the nonperiodic low frequency parts of signals. After this the signals may be compared by the methods outlined above, with particular reference to their correlated parts.

Certain types of output may best be presented in the form of rather unusual graphical displays. In particular:

(1) Plots of power per octave against the logarithm of frequency may be nested together to show the relative intensities of different types of variation over a wide range of frequencies.

(2) A two dimensional histogram could be used to show display the relative frequencies of occurrence of events in relation to their duration and mean number of oscillations.

Figure 17:
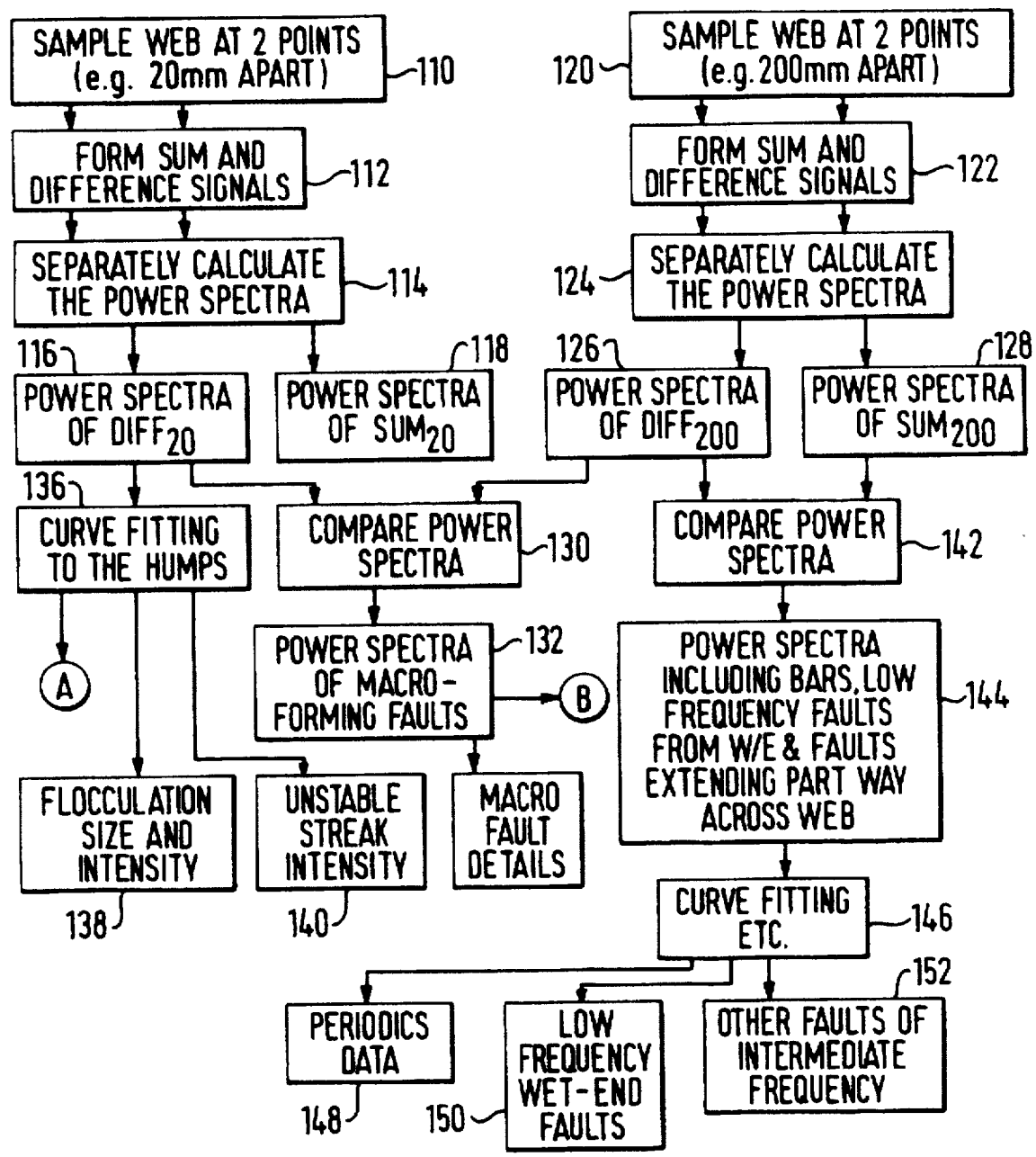
FIG. 17 shows schematically the calculations that may be carried out in one preferred embodiment of the invention (without using dual channel spectral analysis)
Figure 18:
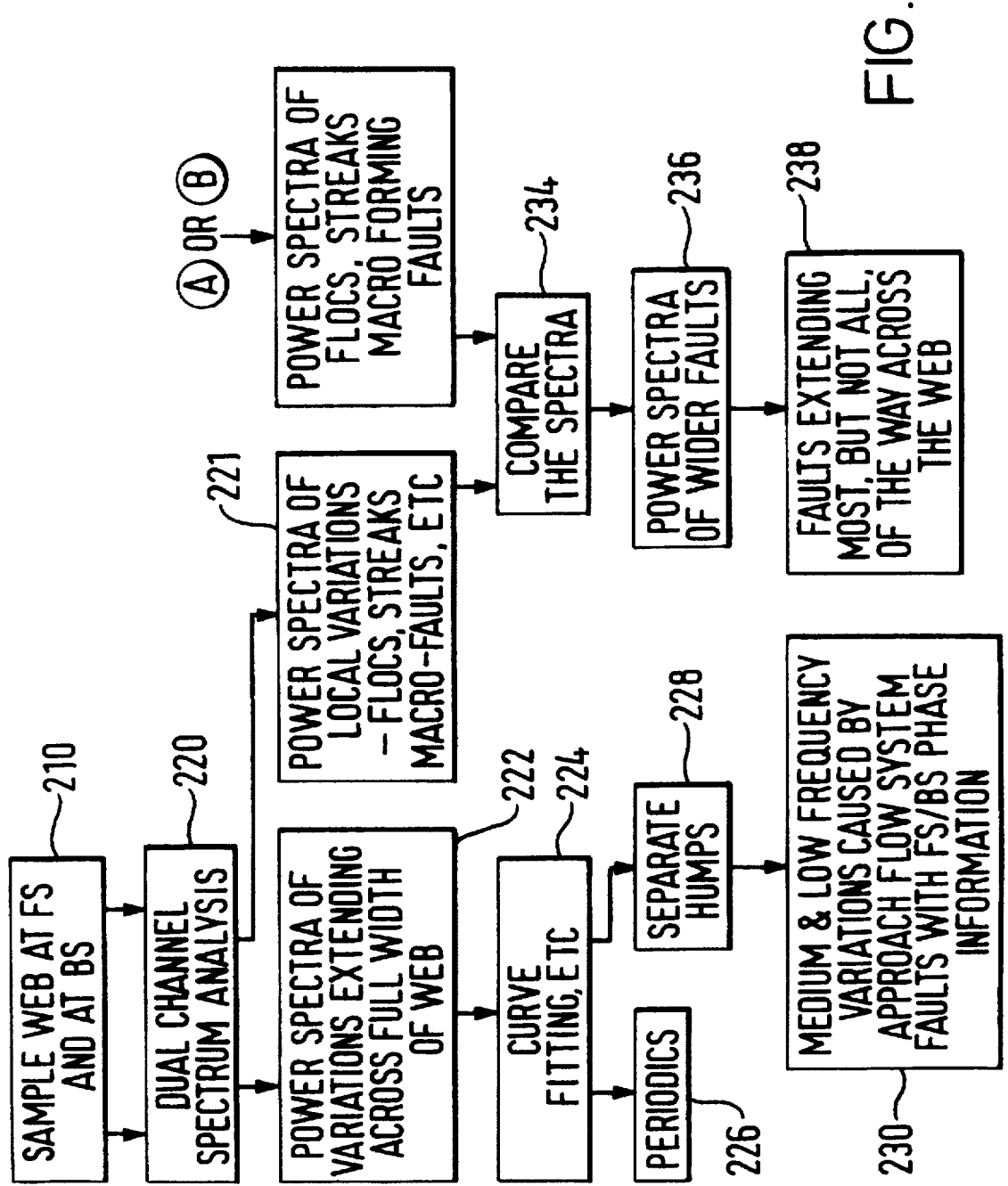
FIG. 18 shows calculations that may be carried out in an embodiment using dual channel spectrum analysis.

FIGS. 17 and 18 show, by way of example, the way in which the calculations may be carried out in two preferred embodiments of the invention. FIG. 17 illustrates how the separation of patterns in the web may be achieved without the use of dual channel spectral analysis. FIG. 18 shows how dual channel spectral analysis may be brought into play, if required.

Turning first to FIG. 17, it will be seen that the analysis starts by sampling 110 the web at two points, for example 20 mm apart. One then calculates at 112 the sum and difference signals from the individual sampled signals. Next, at 114 the power spectra of the sum and differences are separately calculated to give a power spectrum of the difference 116 and a power spectrum of the sum 118. In the figure, the subscript 20 indicates the spacing of the original sample points.

At the same time and in a similar manner, the web is also sampled 120 at two other points, for example 200 mm apart. The sum and difference signals are then calculated at step 122, and the power spectra at 124. One thus obtains the power spectrum of the difference 126 and the power spectrum of the sum 128. The subscript 200 indicates the spacing of the sampling points.

At step 130 the $DIFF_{20}$ and $DIFF_{200}$ are subtracted, leaving one with a power spectrum 132 of macro-forming faults. From this power spectrum, one can determine the details 134 of the macro-forming faults.

In this particular embodiment, the power spectrum of $SUM_{20}$ is ignored. However, curve fitting is carried out to the humps of the power spectrum of $DIFF_{20}$ at step 136, and depending upon the size of humps one thus obtains details of the flocculation size and intensity 138 and on the unstable streak intensity 140.

At step 142, the power spectra of $DIFF_{200}$ and $SUM_{200}$ are subtracted to give a power spectrum 144 representative of bars (periodics), low frequency faults from the wet end, and faults extending partway across the web. At step 146, curve fitting is carried out on this power spectrum, and spikes and humps separated out. This provides data on spikes 148, low frequency wet end faults 150 and other faults of intermediate frequency 152.

Turning now to FIG. 18, it will now be described how dual channel spectrum analysis can be used to provide further information.

The analysis starts at step 210 by sampling the web at two separate points, preferably at the front side and at the back side. Dual channel spectrum analysis 220 is then carried out on the individual sampled signals. From that analysis one obtains two-power spectra: a power spectrum 222 of the variations extending across the full width of the web; and a power spectrum 221 of local variations such as flocculation, streaks, macro-forming faults, and faults which are wider than macro-forming faults but which do not extend across the full width of the web.

At step 224, curve fitting is applied to the power spectrum 222, to separate the spikes. This provides information on periodics 226. Once the spikes have been separated, the humps in the power spectrum may be separated as well, at step 228, providing information on medium and low frequency variations from the wet end, along with front side/back side phase difference information.

From the calculations already carried out in FIG. 17 (for example at points A or B), one can calculate the power spectrum 232 of flocs, streaks and/or macro-forming faults. This power spectrum 232 is then subtracted at step 234 from the power spectrum 221 to provide at 236 a power spectrum of wider faults. This provides information 238 on faults which extend most, but not all, of the way across the web.

It will be appreciated that in FIGS. 17 and 18, the distance in the cross direction between the samples may be determined by trial and error. In FIG. 17, for example, the 20 mm spacing suggested at step 110 is determined experimentally, according to the particular paper machine in question and the effects one is looking for. The skilled man will appreciate that the spacing can be determined experimentally by calculating the cross correlation between the signals.

I claim:

1. A method of analyzing variations in a moving web comprising the steps of:

(a) repeatedly or continuously sampling the variations in a characteristic of the web at each of a plurality of inspection locations spaced apart across the web to produce a corresponding plurality of raw data signals;

(b) determining from the raw data signals a plurality of intermediate signals, at least one intermediate signal being representative of either a weighted or unweighted additive or subtractive combination of two or more of the raw data signals;

(c) calculating a power spectrum for each of the intermediate signals;

(d) subtracting one of either a weighted or unweighted pair of said power spectra from the other of the pair to produce a variation output; and, (e) determining the variations in the sampled web characteristic according to the variation output.

2. The method of claim 1 further including the step of calculating the auto-correlation of either at least one of the intermediate signals or at least one of the raw data signals.

3. The method of claim 1 further including the step of calculating the cross-correlation of either at least one pair of the intermediate signals or at least one pair of the raw data signals.

4. The method of claim 1 further including the step of calculating the dual channel Fourier transform of either at least one pair of the intermediate signals or at least one pair of the raw data signals.

5. The method of claim 1 further including the steps of repeatedly or continuously sampling the variations in a machine characteristic of a machine which is manufacturing the web; and, comparing the variations in the machine characteristic either with the variation output or with one of the intermediate signals.

6. The method of claim 5 wherein the said comparison comprises the step of determining the cross-correlation between the sampled variations in the machine characteristic and either the variation output or one of the intermediate signals.

7. The method of claim 5 further including the step of determining the machine fault or type of machine fault likely to have caused the sampled variations in the web characteristic according to the result of the said comparison.

8. The method of claim 6 further including the step of determining the machine fault or type of machine fault likely to have caused the sampled variations in the web characteristic according to the result of the said comparison.

9. An apparatus for monitoring variations in a moving web comprising:
   (a) sampling means for repeatedly or continuously sampling variations in a characteristic of the web at each of a plurality of inspection locations spaced apart across the web to produce a corresponding plurality of raw data signals;
   (b) determining means for determining from the raw data signals a plurality of intermediate signals, at least one intermediate signal being representative of either a weighted or unweighted additive or subtractive combination of two or more of the raw data signals;
   (c) operating means for calculating a power spectrum for each of the intermediate signals and for subtracting one of either a weighted or unweighted pair of said power spectra from the other of the pair to produce a variation output; and,
   (d) output calculation means for determining the variations in the sampled web characteristics according to the variation output.

10. The apparatus of claim 9 wherein the operating means comprises means for calculating the auto-correlation of either at least one of the intermediate signals or at least one of the raw data signals.

11. The apparatus of claim 10 wherein the operating means comprises means for calculating the cross-correlation of either at least one pair of the intermediate signals or at least one pair of the raw data signals.

12. The apparatus of claim 10 wherein the operating means comprises means for calculating the dual channel Fourier transform either of at least one pair of the intermediate signals or of at least one pair of the raw data signals.

13. The apparatus of claim 10 further including machine variation sampling means for repeatedly or continuously sampling the variations in a machine characteristic of a machine which is manufacturing the web and comparison means for comparing the variations in the machine characteristic with either the variation output or one of the intermediate signals.

14. The apparatus of claim 13 wherein the comparison means comprises means for determining the cross-correlation between the sampled variations in the machine characteristic and either the variation output or one of the intermediate signals.

15. The apparatus of claim 13 further including machine fault determining means for determining either the machine fault or type of machine fault likely to have caused the sampled variations in the web characteristic according to an output of the comparison means.

16. The apparatus of claims 9 wherein the sampling means are spaced in both the direction of motion of the web and the direction across the web.

17. The apparatus of claim 9 wherein the sampling means are spaced in a straight line across the web.

18. The apparatus of claim 9 wherein the sampling means are optical lookers arranged to detect variations in light reflected from the web.

19. The apparatus of claim 9 wherein the sampling means are optical lookers arranged to detect variations in light transmitted through the web.

20. The apparatus of claim 9 wherein the outputs of the sampling means are optical, the raw data signals being combined additively by combining the light outputs from two or more of the sampling means.

21. The apparatus of claim 9 wherein the raw data signals are digitized before combination.

22. The apparatus of claim 9 wherein the sampling means are adjustable across the width of the web.

23. The apparatus of claim 9 wherein the web is a paper web.

* * * * *